United States Patent [19]
Batzdorff et al.

[11] Patent Number: 5,220,308
[45] Date of Patent: Jun. 15, 1993

[54] JOINT EXCURSION MONITOR

[76] Inventors: Jonathan R. Batzdorff; Alfred Batzdorff, both of 50 Montgomery Dr., Santa Rosa, Calif. 95404

[21] Appl. No.: 753,604
[22] Filed: Aug. 30, 1991
[51] Int. Cl.[5] .................. G08B 23/00; A61B 5/103; H01H 19/20; G01C 21/00
[52] U.S. Cl. .................... 340/573; 128/782; 200/570; 377/24.2
[58] Field of Search .............. 340/573, 686, 691, 671; 128/782, 774, 80 C; 200/DIG. 2, 570–571; 377/24.2; 602/26

[56] References Cited

U.S. PATENT DOCUMENTS

| 4,436,099 | 3/1984 | Raftopoulos | 128/782 |
| 4,557,275 | 12/1985 | Dempsey, Jr. | 128/782 |
| 4,834,057 | 5/1989 | McLeod, Jr. | 128/782 |
| 5,027,688 | 7/1991 | Suzuki et al. | 128/782 X |

FOREIGN PATENT DOCUMENTS

| 0596235 | 3/1978 | U.S.S.R. | 128/782 |
| 0997674 | 2/1983 | U.S.S.R. | 128/782 |

OTHER PUBLICATIONS

Biomechanics, "Total Motion Knee Goniometry", vol. 10, No. 3, pp. 183–193, 1977.

Primary Examiner—Jin F. Ng
Assistant Examiner—Thomas J. Mullen, Jr.
Attorney, Agent, or Firm—Larry D. Johnson

[57] ABSTRACT

A joint excursion monitor device which, when strapped onto a person's leg, can monitor a pre-set limit of joint movement, and when that pre-set limit is reached, generate a signal. When set to a point just beyond the allowable limit, this signal may be used to alert the wearer that he has exceeded the allowable range. Alternatively, when set to a point just inside the allowable limit, this signal may alert the wearer that the desired goal has been reached. The device may also count the total number of joint excursions. An alternate embodiment additionally monitors a second plane of joint motion, generally perpendicular to the first plane of motion, and similarly initiates an alarm signal in the event that the wearer should exceed a pre-set allowance.

10 Claims, 9 Drawing Sheets

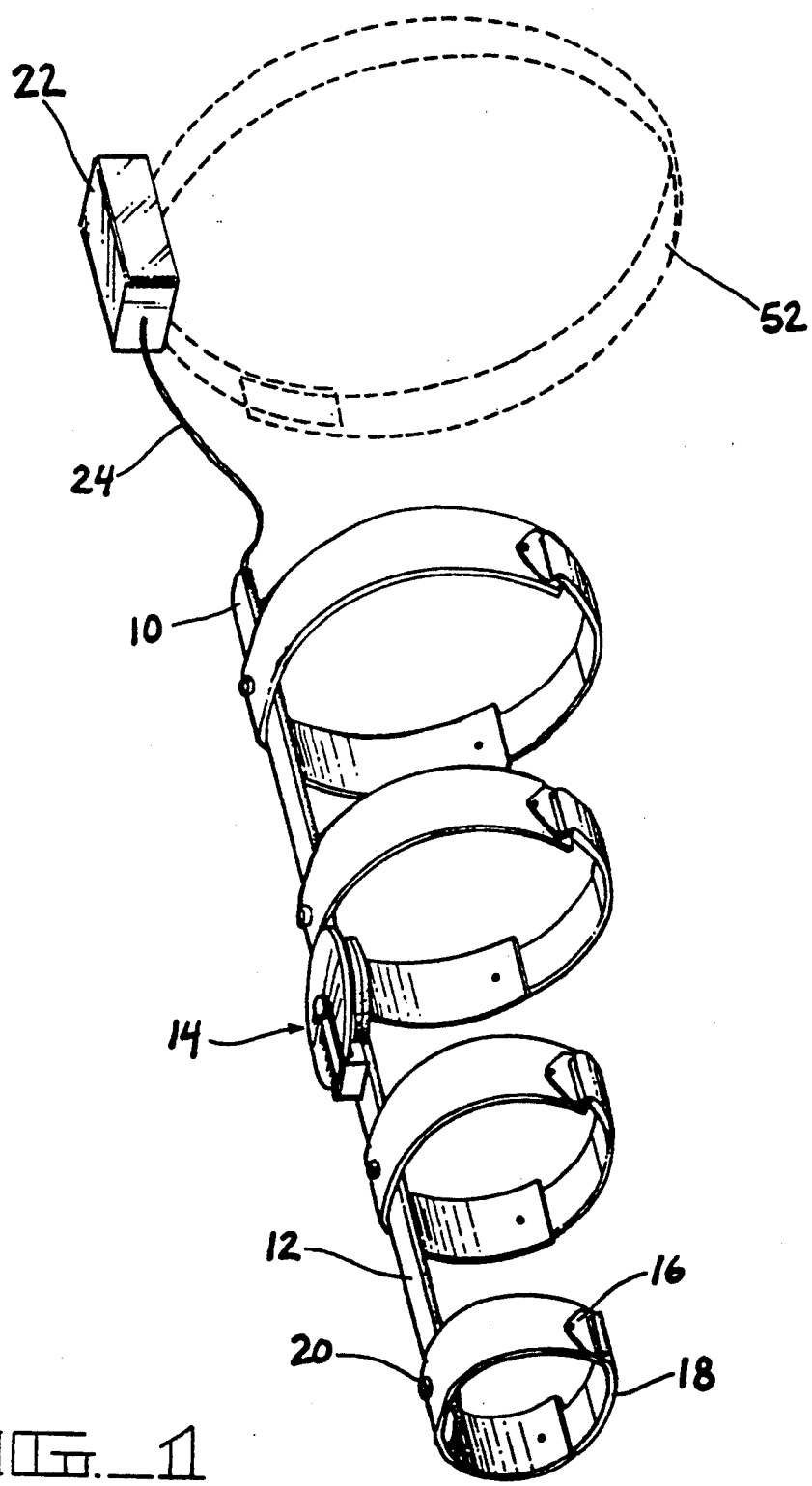
FIG._1

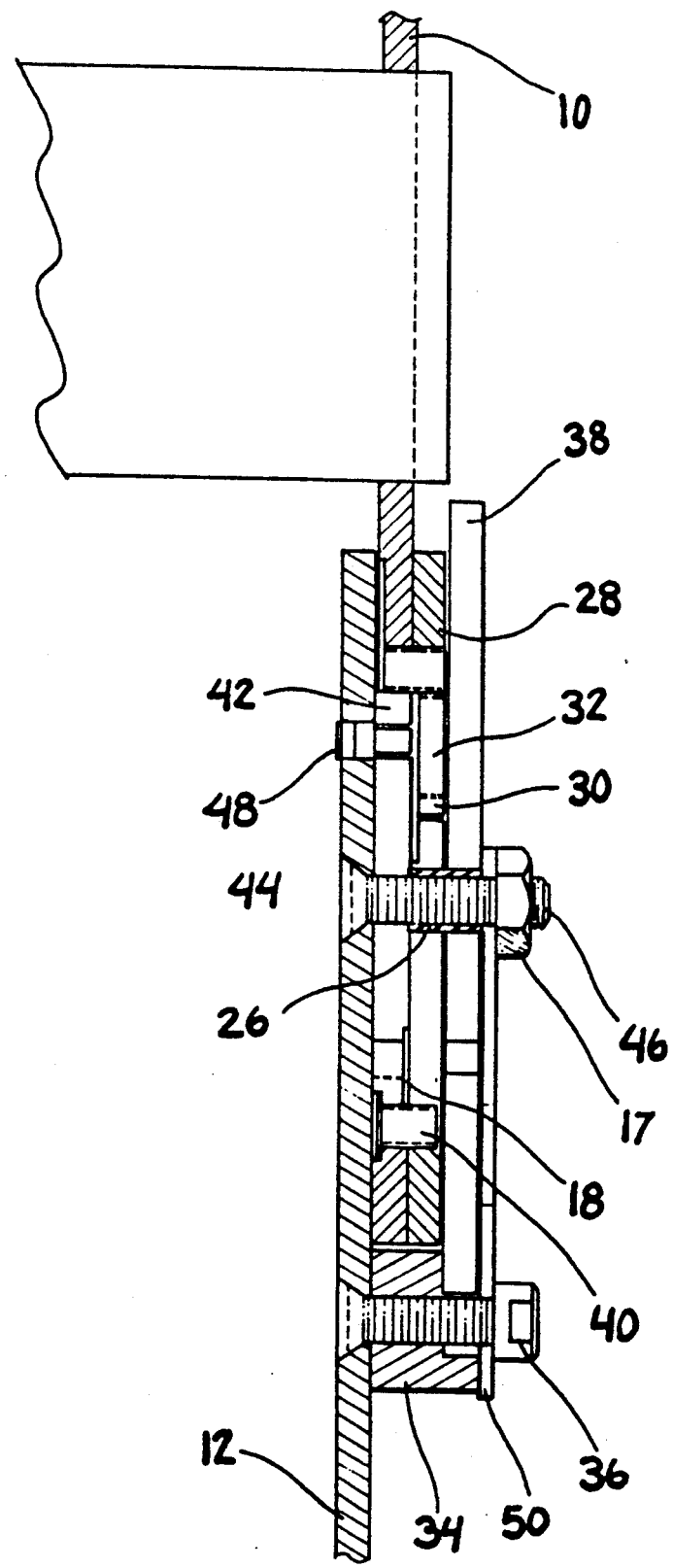
FIG_2

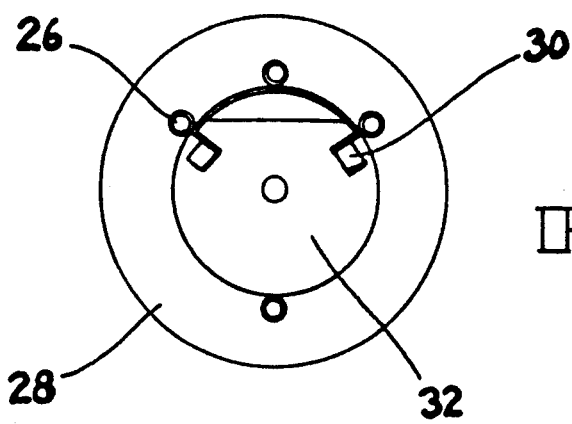
FIG._3
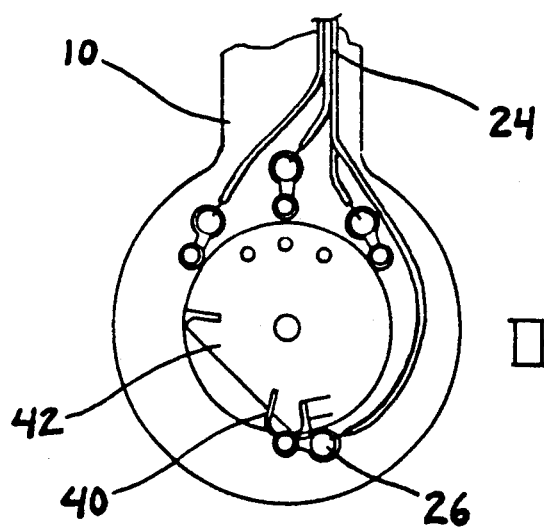
FIG._4
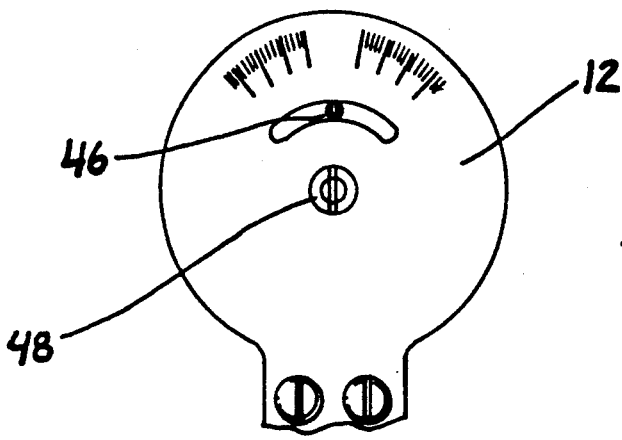
FIG._5

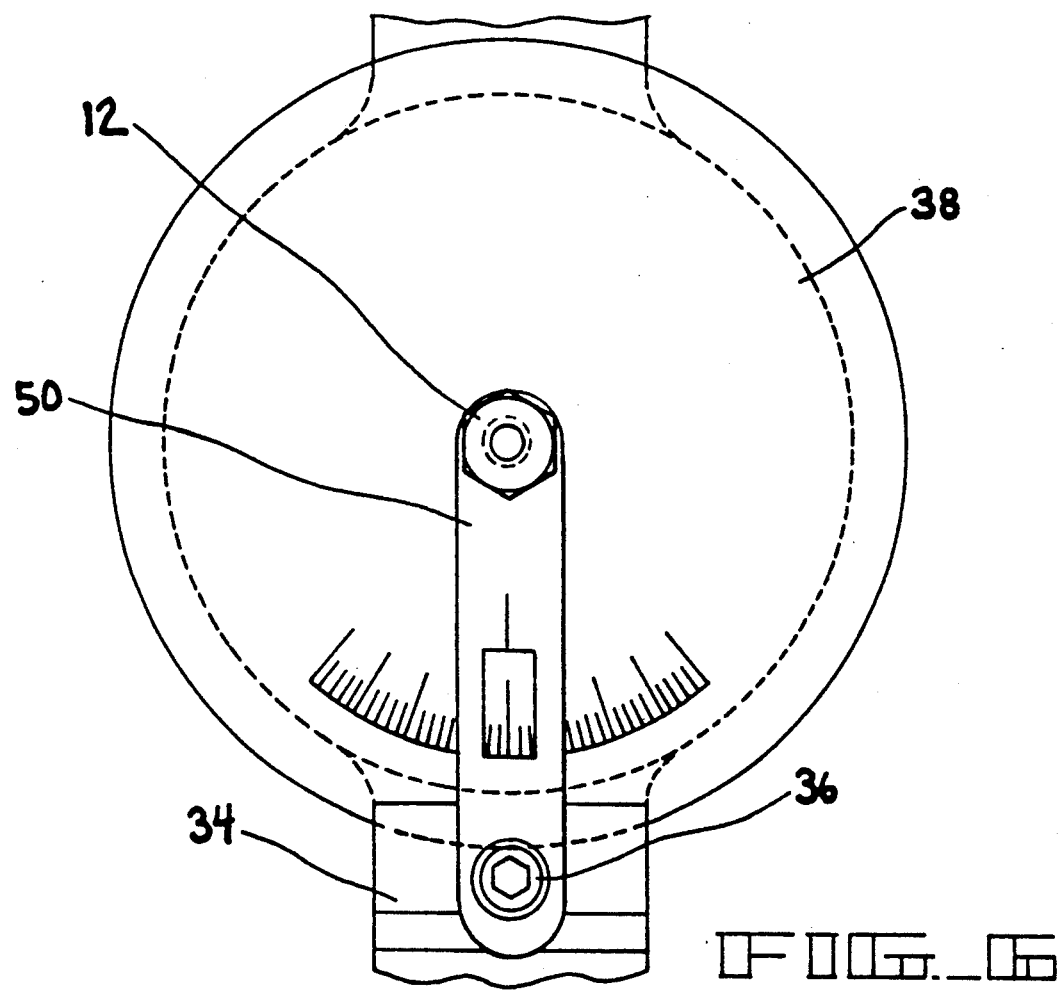
FIG_6
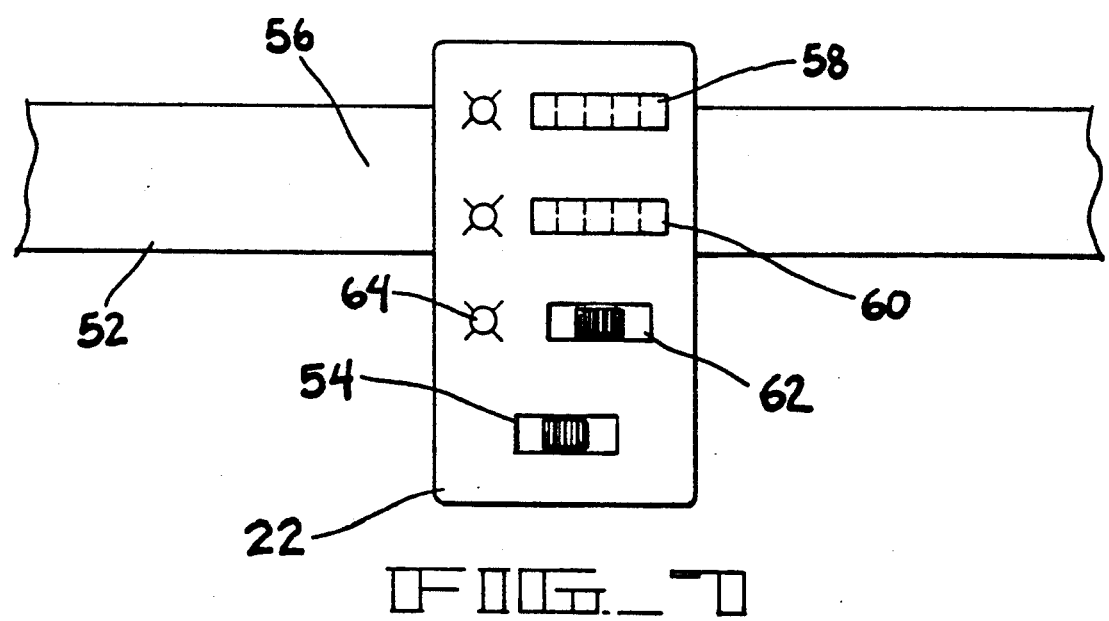
FIG_7

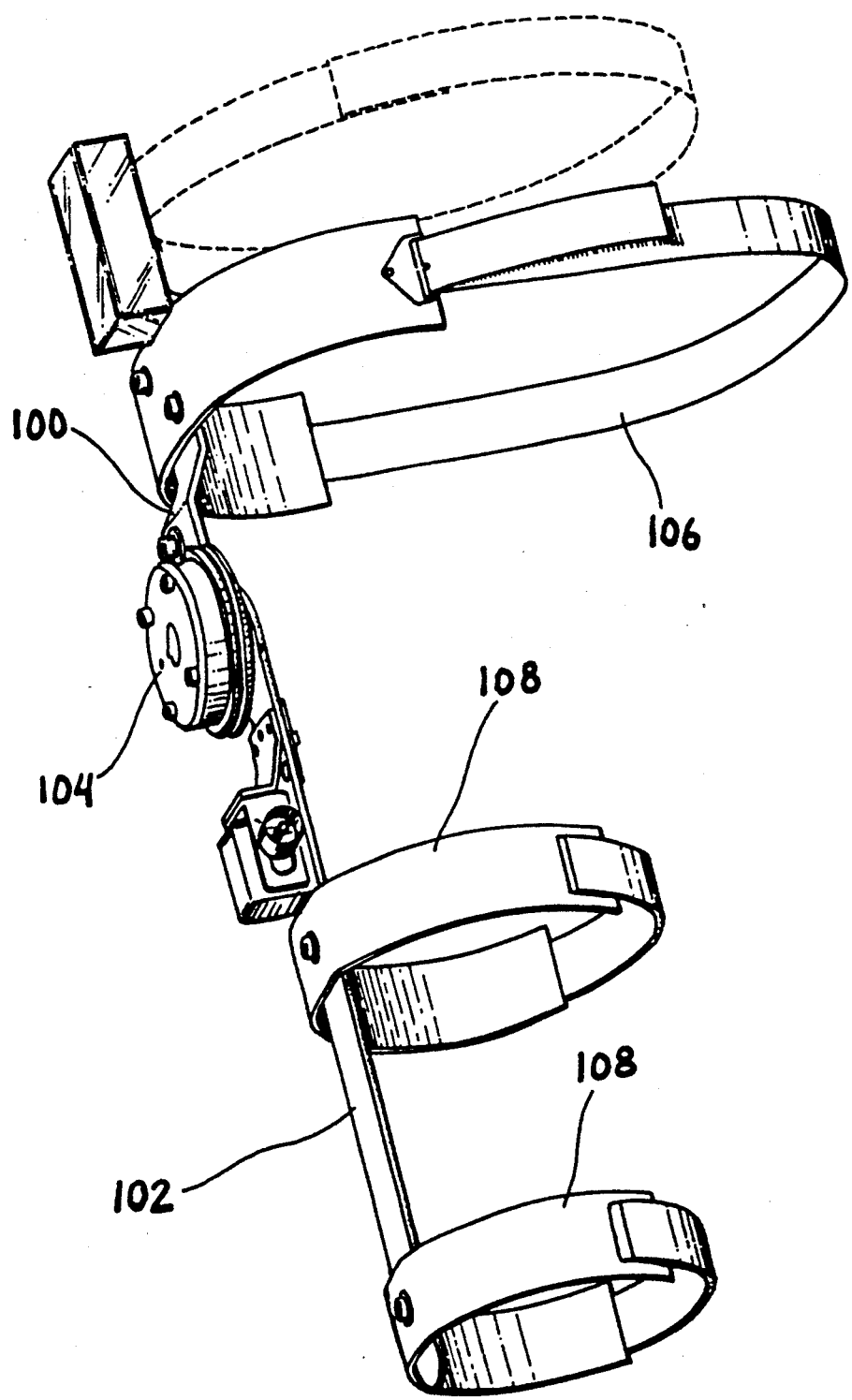
FIG._8

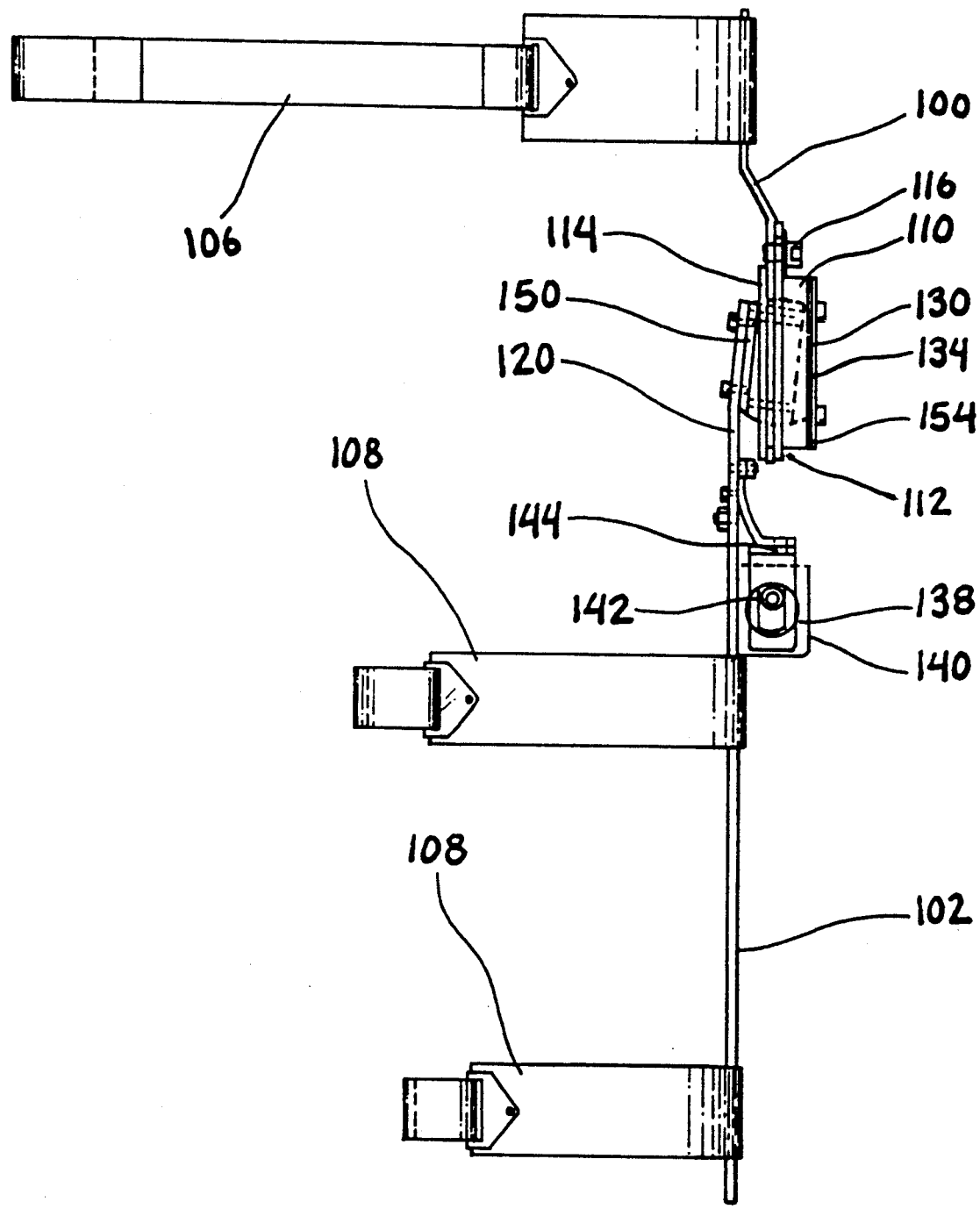
FIG._9

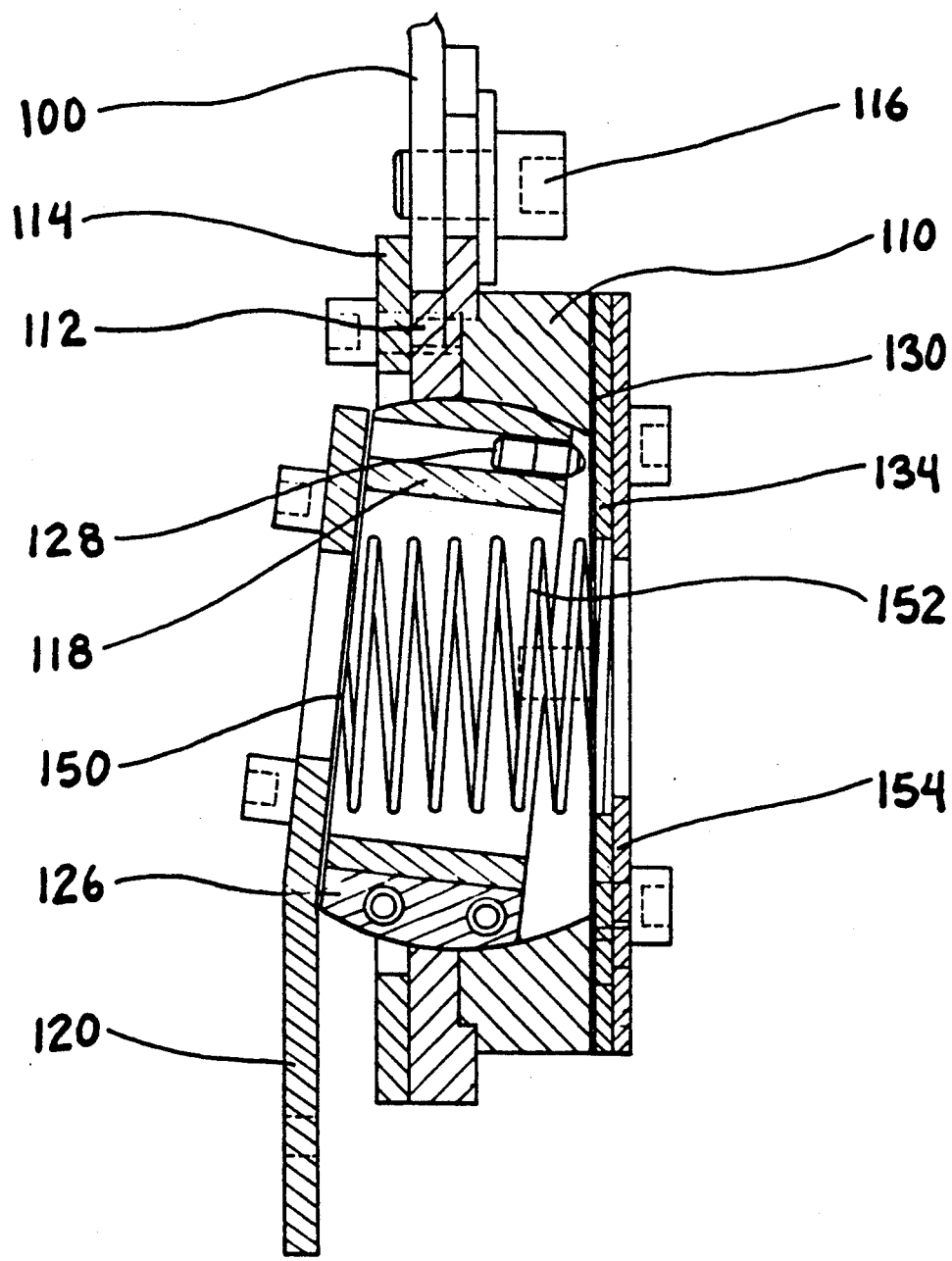
FIG._10

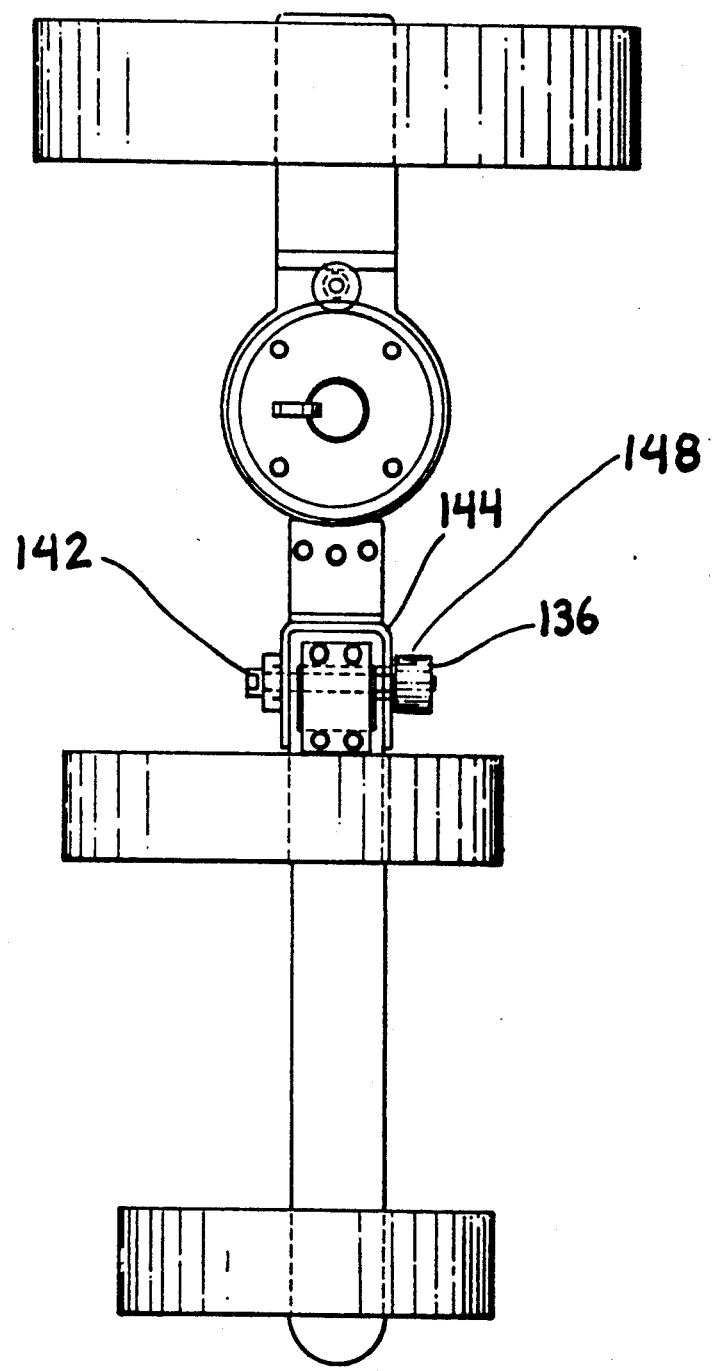
FIG_11

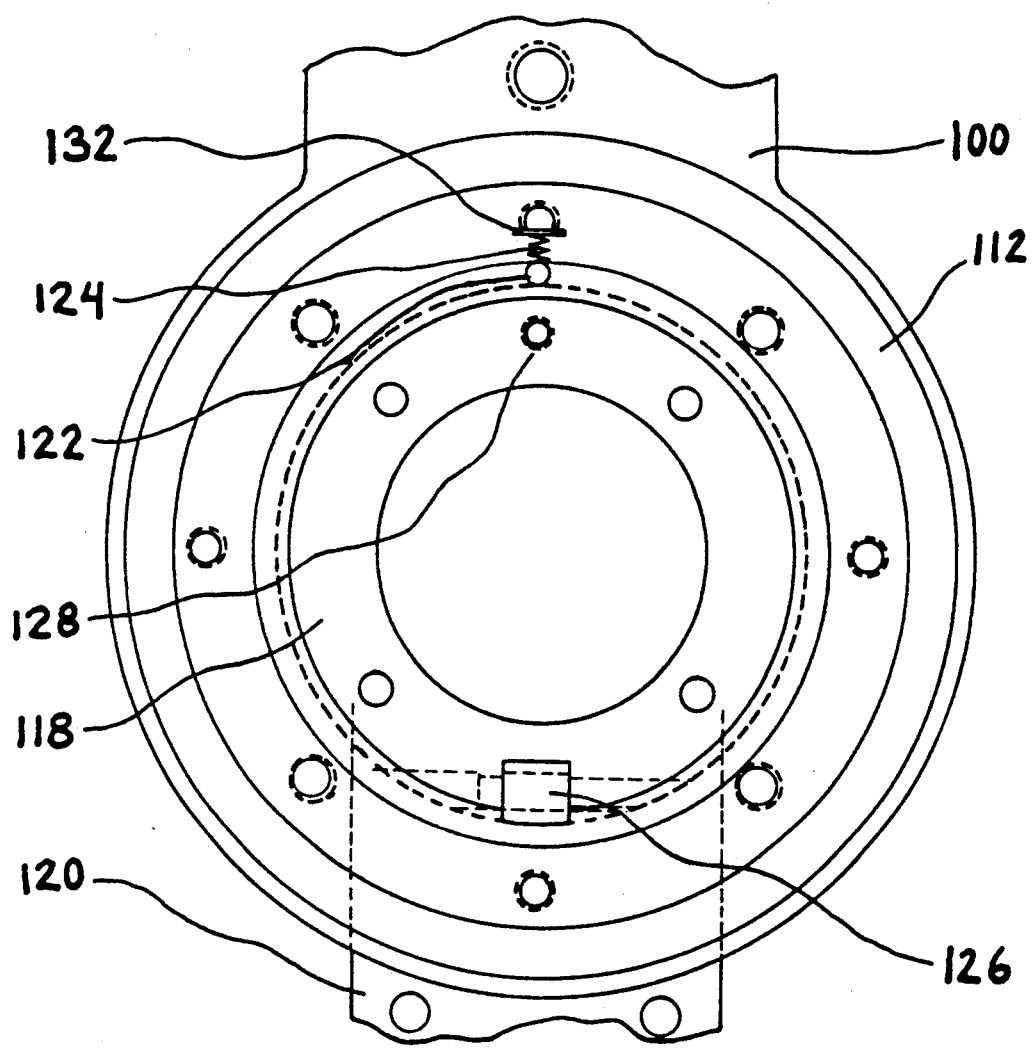
FIG._12
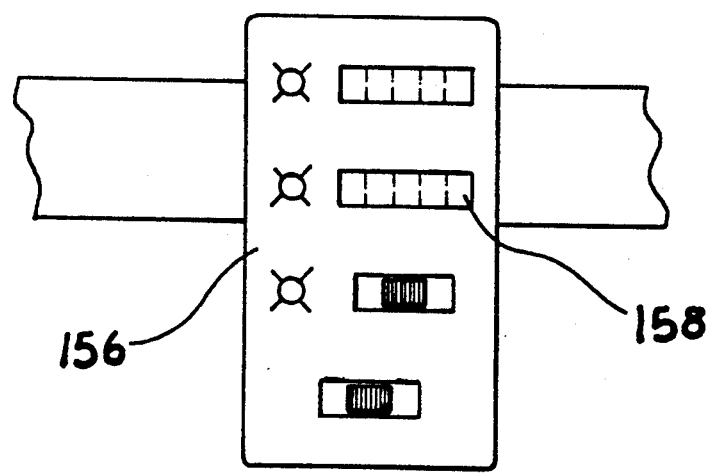
FIG._13

JOINT EXCURSION MONITOR

BACKGROUND OF THE INVENTION

1. Field of the Invention

This invention relates generally to anatomical monitoring devices, and more specifically to an improved device to monitor a pre-set limit of joint movement.

2. Description of the Prior Art

Devices that monitor physical activity are well known. Some such devices provide an alarm signal to warn if the wearer bends beyond an acceptable limit, or falls to a prone position. Others measure strain in a selected exercising region. Still others measure knee motion during exercise. However, no known devices provide a simple, accurate monitor to measure specific joint excursions for use in rehabilitation and training.

SUMMARY OF THE INVENTION

The joint excursion monitor of this invention provides a device which, when strapped onto a person's leg (or other body part), can monitor a pre-set limit of joint movement. When that pre-set limit is reached, the device will generate a signal. When set to a point just beyond the allowable limit, this signal may be used to alert the wearer (e.g., one who is to be protected from excess motion) that he has exceeded the allowable range. Alternatively, when set to a point just inside the allowable limit, this signal may alert the wearer (e.g., one who is training to reach further) that the desired goal has been reached. In addition, means are provided to count the total number of joint excursions.

An alternate embodiment additionally monitors a second plane of joint motion, generally perpendicular to the first plane of motion, and similarly initiates an alarm signal in the event that the wearer should exceed a pre-set allowance (e.g., an adduction monitor to warn if the leg has been flexed too far inward). Such an embodiment is particularly well suited for controlling hip position after surgery and during rehabilitation.

BRIEF DESCRIPTION OF THE DRAWINGS

FIG. 1 is a perspective view of a joint excursion monitor of this invention;

FIG. 2 is an enlarged side elevation cross-sectional view of the center section of the joint excursion monitor of FIG. 1;

FIG. 3 is a front elevation view of the (internal) limit contacts portion of the center section of the joint excursion monitor of FIG. 1;

FIG. 4 is a front elevation view of the (internal) counter contacts portion of the center section of the joint excursion monitor of FIG. 1;

FIG. 5 is a rear elevation view of the center section of the joint excursion monitor of FIG. 1;

FIG. 6 is an enlarged front elevation view of the center section of the joint excursion monitor of FIG. 1;

FIG. 7 is a front elevation view of the signal box portion of the joint excursion monitor of FIG. 1;

FIG. 8 is a perspective view of a dual-plane joint excursion monitor of this invention;

FIG. 9 is a side elevation view of the dual-plane joint excursion monitor of FIG. 8;

FIG. 10 is an enlarged side elevation cross-sectional view of the center section of the dual-plane joint excursion monitor of FIG. 8;

FIG. 11 is a front elevation view of the dual-plane joint excursion monitor of FIG. 8;

FIG. 12 is an enlarged front elevation view of the (internal) contacts portion of the center section of the dual-plane joint excursion monitor of FIG. 8; and FIG. 13 is a front elevation view of the signal box portion of the dual-plane joint excursion monitor of FIG. 8.

DETAILED DESCRIPTION OF A PREFERRED EMBODIMENT

FIG. 1 is a perspective view of a joint excursion monitor of this invention illustrating an upper bar 10 and lower bar 12 hinged to each other at a center section 14, where the upper bar 10 is bored to fit a bearing disk (described infra) which is securely mounted to the lower bar 12, thus permitting free rotation of one bar with respect to the other. These bars are strapped to two segments of a jointed limb (as, for example, the thigh and calf of a person's leg), with the device's center section hinge point placed on the axis of the joint to be monitored (as, for example, the knee joint). When the electric contacts, which are mounted on the bars, are closed, they will generate the desired signals.

Plastic hoops 16, sized to fit the wearer, are secured to the limb by means of VELCRO brand hook and loop fastener straps 18. These hoop-and-strap assemblies are attached to the bars 10, 12 by means of suitable fasteners 20, as, for instance, carriage bolts with washers and hexagon nuts. The semi-rigid plastic hoops are sized to fit snugly on the limb and, when securely fastened, will prevent movement of the device with respect to the limb. The above described means of attachment makes the hoop assemblies readily removable and interchangeable. This can be an essential feature, as the hoops are preferably asymmetrical, and have to be installed in alternate directions to make the device suitable for the limbs on either side of the wearer. In addition, the hoop assemblies may be interchanged with assemblies of alternate size ranges to render the device suitable for wearers of different body build.

Limit and/or counting signals are sent from the electrical contacts to signal box 22 via cable 24, as described infra.

Limit signals: While there are many ways in which electric contacts may be executed (as, for example, by means of cam operated limit switches), in the particular execution here described (and as shown in FIG. 3 and FIG. 4), electric contacts 26 are imbedded on the periphery of the contact ring 28, which is mounted to the upper bar 10. A contact strip 30 is imbedded in the bearing disk 32. The center contact of the three-contact group is connected to one side of the switching circuit, and a selector switch is utilized to determine which of the two lateral contacts will be connected to the other side (depending on the direction of rotation). As soon as the contact strip 30 touches both the center and the "hot" lateral contact, the circuit is completed and the limit signal is generated.

While the device is in operation, the contact disk 32 must be firmly mounted to the lower bar 12, but to program the exact threshold point for generation of the limit signal (switch closure) it must be adjustable. As shown in view FIG. 2, a clamp block 34 is mounted on the bar 12 and a socket screw 36 is used to clamp the cover plate 38 securely to the bar 12. As the contact disk 32 is an integral part of (or securely mounted to)

the cover plate 38, it too, is securely mounted with respect to the bar.

Counting signals: As shown in FIG. 4, electric contacts 26 are imbedded on the periphery of the bore in the upper bar 10. A contact strip 40 is imbedded in the bearing disk 42. This contact strip is electrically connected to the limit contact strip 30 by means of the contact disk 44 (shown in FIG. 2), and thus to one side of the counting signal generating circuit. The contact 26 shown in FIG. 4 is connected to the other side of the counting circuit. As soon as the contact strip 40 touches that terminal, the circuit is completed and the counting pulse is generated.

While the device is in operation, the contact disk 42 must be firmly mounted to the lower bar 12, but to program a point which is reliably within the excursion range for generation of the counting signal (switch closure), it must be adjustable. As shown in FIG. 2 and FIG. 5, after the nut 17 of the center screw 46 is loosened, a pin 48 in the contact disk 42 can be utilized to move it with respect to the bar 12. Thereafter, the nut 17 of the center screw 46 is tightened.

As shown in FIG. 6, the cover plate 38 is inscribed with angle designations which, if used in conjunction with the pointer 50, facilitate accurate setting of the contact disk.

The upper bar 10, to which the contacts are mounted, also contains the cable 24 which connects the contacts to the signal box 22 (FIG. 7), which may be worn on the user's belt. The signal box consists of a small enclosure, worn on the user's belt 52. It contains a socket suitable to receive a connector at the end of cable 24. The signal box preferably contains the following devices:

A selector switch 54 to select the appropriate limit contact, dependent on the direction of rotation, i.e., on which side of the wearer the monitoring device is installed.

A signal generator 56. While any type of audible, visible or tactile signal may be generated, the one chosen in this instance is a beeper, and may additionally include a signal generator on-off switch (not shown).

An excursion counter 58 to record the total number of joint excursions.

A limit counter 60 to record the number of instances the limit circuit has been closed, i.e., the pre-determined limit has been reached.

A battery (not shown) suitable for powering the counters and the signal generator.

A power on-off switch 62 with a power-on pilot light 64.

The signal box may further include any of a variety of optional devices, including, but not necessarily limited to a computer to calculate the percentage of "limit" signals compared to the total number of excursions; a computer with an internal clock to calculate the frequency of excursions; a storage device with a dumping circuit to facilitate the transfer of the data to a computer or other external device; and a signal transmitter to transmit the pulse signals directly to an external device suitable to perform all counting and computing functions.

FIG. 8 is a perspective view of a dual-plane joint excursion monitor of this invention, illustrating upper bar 100 and lower bar 10 hinged to each other by the ball-type joint 104. The upper bar is strapped to the patient's hip by means of the hip strap assembly 106, and the lower bar is strapped to the patient's leg by means of the leg strap assembly 108, in analogous fashion to the assemblies described supra, and as to locate the device's hinge point on the axis of the hip joint to be monitored. When the electric contacts, which are integral to the device, are actuated, they will generate the desired signals.

FIGS. 9, 10, 11, and 12 are a series of views of the dual-plane joint excursion monitor of FIG. 8. Mounted on the upper bar 100 is the two-part stator 110, 112 (FIG. 10). The lower half of the stator fits into a bore in the upper bar where it is free to rotate, but retained by the retaining ring 114. After the stator is adjusted to generate the excursion signal at the desired point, it is clamped to the upper bar by means of the clamping screw 116. The inside of the stator has a spherical bore to accommodate the rotor 118.

The rotor is mounted on the mounting plate 120, which is part of the lower bar assembly. When the metallic rotor rotates, it makes contact with a spring-loaded ball 122, 124 (FIG. 12) which is mounted in the plastic stator 110. However, the metallic rotor is supplied with a non-metallic insert 126, and when the stator rotates to a point where the plastic insert reaches the ball-contact, the current flow is interrupted.

Mounted on the rotor is a plunger contact 128 (FIG. 10). When the leg adduction reaches the pre-set limit, this plunger contact makes contact with the adduction signal disk 130, thus completing a circuit and initiating an alarm signal.

Limit signals (excursion monitor): The excursion monitor signal is initiated when current flow to a normally energized relay is interrupted. This occurs when plastic insert 126 of the rotor 118 reaches the ball contact 122. As the ball contact is mounted in the stator 110, the excursion limit is pre-adjusted by rotation of the stator with respect to the upper bar 100, and then clamping it in place with the clamp screw 116. The current flow from the contact ball 122 occur via the spring 124 and the contact strip 132. One lead of the cable, which enters the device through its center bore, is attached to the upper end of the contact strip.

Adduction alarm: The adduction alarm signal is initiated when current flow is established by the plunger 128 touching the contact disk 130, which is separated from the metallic cover 154 by the insulator 134. As the rotor 118 is mounted on a mounting plate 120 which is hinged to the lower bar 102, adjustment of the angle between the mounting plate and the lower bar will pre-set the adduction limit. This adjustment is made by rotation of the knurled cap 136 (FIG. 11) which will, in turn, rotate the eccentric 138 (FIG. 9) in its bearing block 140 which is mounted on the lower bar. The shoulder screw 142 is retained by the bracket 144 which is mounted to the stator mounting plate 120. After the eccentric is adjusted to suit, it is clamped by tightening of the shoulder screw 142. Friction washers 148 will further assure the reliability of the clamping action.

The current flow to the plunger 128 (FIG. 10) occurs through the rotor 118 and the lower spring disc 150 and the spring 152 to the cover plate 154 which is fitted with a terminal for the cable which enters the device through the center bore.

FIG. 13 is a front elevation view of the signal box portion 156 of the dual-plane joint excursion monitor of FIG. 8. This signal box is analogous to the single-plane joint excursion monitor signal box described supra. In addition, the dual-plane joint excursion monitor signal box may include:

A pc-board type miniature relay to control the excursion limit signal (not shown).

An adduction alarm signal generator 158. While any type of audible, visible, or tactile signal may be generated, the one chosen in this instance is a beeper. In an alternate approach, one signal generator could be employed for both of the stated purposes, if the pitch can be differentiated by inclusion of a resistor in one of the two circuits.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A joint excursion monitor apparatus to measure relative movement of two segments of a jointed limb, said monitor apparatus comprising:
   a first bar portion having a strap assembly for releasable attachment to one segment of a jointed limb;
   a second bar portion having a strap assembly for releasable attachment to the other segment of said jointed limb;
   a hinge portion connecting said first bar portion to said second bar portion proximate the axis of the limb joint to be monitored, said hinge portion including a first bar portion electrical contact and a second bar portion electrical contact, said first and second bar portion electrical contacts being adjustable relative to one another and conditioned to close when said first bar portion and said second bar portion are moved to a first selected angular relationship;
   circuit means for generating an alarm signal when said first and second bar portion electrical contacts are closed; and
   a signal box for displaying excursion count data.

2. The joint monitor of claim 1 further including second circuit means for generating a second alarm signal when said first bar portion and said second bar portion are moved to a second selected angular relationship in a plane generally perpendicular to said first selected angular relationship.

3. The joint monitor of claim 1 wherein said strap assemblies comprise asymmetrical plastic hoops.

4. The joint monitor of claim 1 wherein said alarm signal comprises an audible sound.

5. The joint monitor of claim 1 wherein said signal box comprises a selector switch.

6. A joint excursion monitor apparatus to measure relation movement of two segments of a jointed limb, said monitor apparatus comprising:
   a first bar portion having a strap assembly for releasable attachment to one segment of a jointed limb;
   a second bar portion having a strap assembly for releasable attachment to the other segment of said jointed limb;
   a hinge portion connecting said first bar portion to said second bar portion proximate the axis of the limb joint to be monitored, said hinge portion including a first bar portion electrical contact and a second bar portion electrical contact, said first and second bar portion electrical contacts being adjustable relative to one another and conditioned to close when said first bar portion and said second bar portion are moved to a first selected angular relationship;
   circuit means for generating an alarm signal when said first and second bar portion electrical contacts are closed; and
   a signal box for displaying limit count data.

7. The joint monitor of claim 6 further including second circuit means for generating a second alarm signal when said first bar portion and said second bar portion are moved to a second selected angular relationship in a plane generally perpendicular to said first selected angular relationship.

8. The joint monitor of claim 6 wherein said strap assemblies comprise asymmetrical plastic hoops.

9. The joint monitor of claim 6 wherein said alarm signal comprises an audible sound.

10. The joint monitor of claim 6 wherein said signal box comprises a selector switch.

* * * * *